United States Patent
Izumi et al.

(10) Patent No.: US 8,945,865 B2
(45) Date of Patent: Feb. 3, 2015

(54) METHOD FOR SCREENING FOR COMPOUND CAPABLE OF ENHANCING OR INHIBITING OATP1B1 TRANSPORT ACTIVITY, AND METHOD FOR DETERMINING EXPRESSION LEVEL OF OATP1B1

(75) Inventors: Saki Izumi, Tsukuba (JP); Takafumi Komori, Tsukuba (JP); Yoshitane Nozaki, Tsukuba (JP)

(73) Assignee: Eisai R&D Management Co., Ltd., Tokyo (JP)

( * ) Notice: Subject to any disclaimer, the term of this patent is extended or adjusted under 35 U.S.C. 154(b) by 0 days.

(21) Appl. No.: 14/003,541

(22) PCT Filed: Mar. 6, 2012

(86) PCT No.: PCT/JP2012/055719
§ 371 (c)(1),
(2), (4) Date: Sep. 6, 2013

(87) PCT Pub. No.: WO2012/121261
PCT Pub. Date: Sep. 13, 2012

(65) Prior Publication Data
US 2014/0024070 A1 Jan. 23, 2014

(30) Foreign Application Priority Data
Mar. 10, 2011 (JP) ................................ P2011-053270

(51) Int. Cl.
*C12Q 1/68* (2006.01)
*G01N 21/64* (2006.01)
*G01N 33/50* (2006.01)
*G01N 33/58* (2006.01)
*G01N 33/68* (2006.01)

(52) U.S. Cl.
CPC ........ *G01N 21/6486* (2013.01); *G01N 33/5008* (2013.01); *G01N 33/582* (2013.01); *G01N 33/6872* (2013.01); *G01N 33/5067* (2013.01); *G01N 2500/00* (2013.01)
USPC ............................. 435/29; 435/6.1; 435/6.17

(58) Field of Classification Search
CPC ... G01N 33/00; G01N 33/48; G01N 33/5044; G01N 33/5067; G01N 33/6872; G01N 33/582; G01N 21/00; G01N 21/62; G01N 21/64; G01N 21/645; G01N 21/6486; C12N 10/00; C12N 2503/00; C12N 2503/02; C12N 2510/00; C12N 2510/02; C12N 5/06; C12N 5/0602; C12N 5/067; C12N 5/0671; C12N 5/0686; C07K 1/00; C07K 14/47
See application file for complete search history.

(56) References Cited

U.S. PATENT DOCUMENTS

2010/0196960 A1* 8/2010 Nezu et al. ................... 435/69.1

FOREIGN PATENT DOCUMENTS

JP    2006-340610    12/2006
JP    2009-225797    10/2009

OTHER PUBLICATIONS

International Preliminary Report on Patentability in PCT App. Ser. No. PCT/JP2012/055719, dated Sep. 19, 2013, 4 pages.
Bednarczyk, D., Fluorescence-based assays for 1-15 the assessment of drug interaction with the human transporters OATP1B1 and OATP1B3, Analytical Biochemistry, vol. 405:50-58 (2010).
Cihlar, et al., "Fluorescence-Based Assay for the Interaction of Small Molecules with the Human Renal Organic Anion Transporter I", Analytical Biochemistry, vol. 283:49-55, (2000).
Giacomini, et al., "Membrane transporters in drug development", Nature Reviews Drug Discovery, vol. 9:215-236 (2010).
Hsiang, et al.,"A Novel Human Hepatic Organic Anion Transporting Polypeptide(OATP2)", J. Biol. Chem., vol. 274:37161-37168, (1999).
Lebel, C. P. et al., Evaluation of the Probe 2',7'-Dichlorofluorescin as an Indicator of Reactive Oxygen Species Formation and Oxidative Stress, Chem. Res. Toxicol., vol. 5:227-231 (1992).
Soars et al., "The pivotal role of hepatocytes in drug discovery", Chemico-Biological Interactions, vol. 168:2-15 (2007).
Yamaguchi, H. et al., Screening of Antibiotics 1-15 That Interact with Organic Anion-Transporting Polypeptides 1B1 and 1B3 Using Fluorescent Probes, Biol. Pharm. Bull., vol. 34(3):389-395 (2011).
Yamaguchi, H. et al., Transport of fluorescent 1-15 chenodeoxycholic acid via the human organic anion transporters OATP1B1 and OATP1B3, Journal of Lipid Research vol. 47:1196-1202 (2006).
International Search Report for PCT/JP2012/055719, dated Apr. 17, 2012, Refs only.
Maciej, J. et al., "Pharmacokienetics of 5 (and 6)-Carboxy-2',7'-Dichlorofluorescein and Its Diacetate Promoiety in the Liver," The Journal of Pharmacology and Experimental Therapeutics, 304(2):801-809 (2003).
Office Action in Chinese application No. 201280022124.9, dated Aug. 14, 2014, 7 pages.

* cited by examiner

*Primary Examiner* — John S Brusca
*Assistant Examiner* — Sharon M Papciak
(74) *Attorney, Agent, or Firm* — Fish & Richardson P.C.

(57) ABSTRACT

The present invention provides a method of screening for a compound that enhances or inhibits the transport activity of OATP1B1, using dichlorofluorescein. The present invention also provides a use of dichlorofluorescein in measurement of the expression level of OATP1B1. The present invention further provides a method for measuring the expression level of OATP1B1 in test cells, using dichlorofluorescein. The present invention further provides a use of a kit including dichlorofluorescein and positive cells expressing OATP1B1 in measurement of the expression level of OATP1B1 in test cells.

13 Claims, 8 Drawing Sheets

Fig.1
(a)
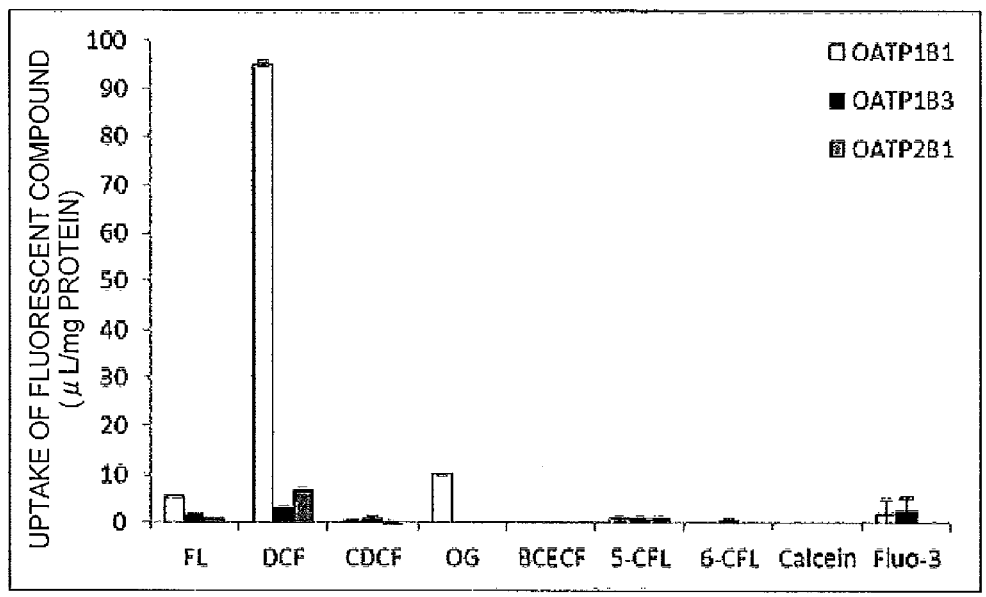
(b)
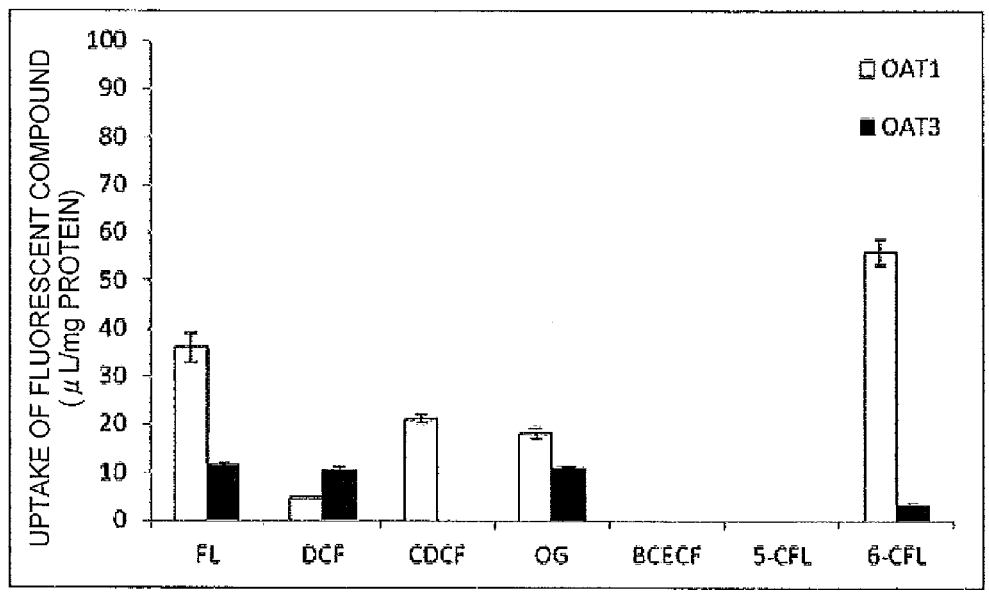

METHOD FOR SCREENING FOR COMPOUND CAPABLE OF ENHANCING OR INHIBITING OATP1B1 TRANSPORT ACTIVITY, AND METHOD FOR DETERMINING EXPRESSION LEVEL OF OATP1B1

TECHNICAL FIELD

The present invention relates to a method, using a fluorescent compound dichlorofluorescein, for screening for a compound that enhances or inhibits the transport activity of OATP1B1 and relates to a method for measuring the expression level of OATP1B1.

BACKGROUND ART

In recent years, it has been increasingly recognized that hepatocytes play important roles in drug discovery. Hepatocytes are indispensable tools for pharmacokinetic studies of drugs, such as prediction of in vivo clearance of drugs or investigation of drug interaction. The molecular mechanisms of various metabolic enzymes and transporters that are expressed in hepatocytes and playing dominant roles in pharmacokinetics (absorption, distribution, metabolism, and excretion) of drugs have been being revealed. Among them, much attention has been paid to the roles of organic anion-transporting polypeptides (OATPs) in the pharmacokinetics of anionic drugs (Non Patent Literature 1).

The OATP family transporters are expressed in various tissues and organs in the body, such as small intestine, kidney, and liver, and among them, OATP1B1 (alias: OATP-C, OATP2, or LST-1), OATP1B3 (alias: OATP-8), and OATP2B1 (alias: OATP-B) are known to be highly expressed in human hepatocytes (Non Patent Literatures 2 and 3). Clinically important drugs such as statins and angiotensin II receptor blockers are known to be taken up by human hepatocytes mainly via OATP1B1, and cyclosporine and rifampicin are known as typical inhibitors of OATP1B1 (Non Patent Literature 2).

It is known that a concomitant use of an OATP1B1 substrate drug with an OATP1B1 inhibitor reduces uptake of the substrate drug into the liver, resulting in increase in the blood level of the substrate drug in clinical settings. Accordingly, evaluation of the drug interaction potential of a test compound via OATP1B1 is very important from the view point of clinical safety. Conventionally, in order to quantitatively evaluate transporter-mediated drug interaction potential of a test compound, an evaluation method (RI method) using a known substrate labeled with a radioisotope is known (Patent Literature 1).

The RI method gives high sensitivity, but is expensive, and also needs caution when handling the samples. Instead, a detection method (fluorescence method), not using any radioisotope, but using a fluorescent compound, is also known. For example, an evaluation method using 6-carboxyfluorescein (6-CFL), which is a good substrate for organic anion transporter 1 (OAT1), has been reported (Non Patent Literature 4).

It can be said that the fluorescence method is easy to operate, is less expensive than the RI method, and has excellent throughput. However, in general, it is difficult to predict whether a compound can or cannot serve as a substrate of a transporter, and, therefore, not many fluorescent compounds that can function as substrates of anion transporters are known. In addition, some conventional fluorescent substrates have disadvantages such as that the detection sensitivity is not necessarily high due to a low fluorescence intensity emitted by the substrate itself, autofluorescence of a test compound, and photobleaching of the fluorescent substrate.

CITATION LIST

Patent Literature

Patent Literature 1: Japanese Patent Application Laid-Open No. 2006-340610

Non Patent Literature

Non Patent Literature 1: Matthew G. Soars, et al., Chemico-Biological Interactions, 168, (2007) pp. 2-15
Non Patent Literature 2: Kathleen M. Giacomini, et al., Nature Reviews Drug Discovery, Vol. 9, pp. 215-236, 2010
Non Patent Literature 3: Bonnie Hsiang, et al., J. Biol. Chem., Vol. 274, pp. 37161-37168, 1999
Non Patent Literature 4: Tomas Cihlar, et al., Analytical Biochemistry, 283, pp. 49-55, 2000

SUMMARY OF INVENTION

Technical Problem

Accordingly, in view of the problems associated with the conventional RI method, it is an object of the present invention to provide a method using a fluorescent compound for screening for a compound that enhances or inhibits the transport activity of OATP1B1, being safe, inexpensive, and easy to operate and allowing detection with sensitivity comparable to that of the RI method, and also to provide a method for measuring the expression level of OATP1B1.

Solution to Problem

In order to solve the above problems, the present inventors have investigated a plurality of fluorescent compounds for their adaptability as substrates of OATPs. As a result, it was revealed that dichlorofluorescein (DCF) is an excellent substrate of OATP1B1, and it was also surprisingly found that the results of evaluation using DCF as a substrate of OATP1B1 are equivalent to those by the conventional RI method, and the present invention was accomplished.

That is, the present invention provides a method of screening for a compound that enhances or inhibits the transport activity of OATP1B1, using dichlorofluorescein.

The method preferably includes a step of preparing cells expressing OATP1B1; a step of bringing dichlorofluorescein and a test compound into contact with the cells; a step of measuring the fluorescence intensity of dichlorofluorescein taken up by the cells; and a step of determining the test compound as a compound that enhances the transport activity of OATP1B1 in a case that the measured fluorescence intensity is higher than that when the test compound is not present and determining the test compound as a compound that inhibits the transport activity of OATP1B1 in a case that the measured fluorescence intensity is lower than that when the test compound is not present.

It is preferable that the cells expressing OATP1B1 in the screening method of the present invention be selected from the group consisting of OATP1B1 forced-expression cells, immortalized human hepatocytes, primary cultured human hepatocytes, freshly isolated human hepatocytes, cryopreserved human hepatocytes, and sandwich-cultured human hepatocytes or be cells overexpressing a protein consisting of the amino acid sequence shown in SEQ ID NO: 1 in the cell membrane or cells transformed with a DNA consisting of the nucleotide sequence shown in SEQ ID NO: 2.

The present invention also provides a use of dichlorofluorescein in measurement of the expression level of OATP1B1.

The present invention also provides a method for measuring the expression level of OATP1B1 in test cells, and the method includes a step of bringing dichlorofluorescein into contact with test cells; a step of measuring the fluorescence intensity of dichlorofluorescein taken up by the test cells; and a step of evaluating the expression level of OATP1B1 in the test cells based on the measured fluorescence intensity.

In the measurement method of the present invention, it is preferable to relatively evaluate the expression level of OATP1B1 in test cells using positive cells expressing OATP1B1 as a control. It is preferable that the positive cells expressing OATP1B1 be selected from the group consisting of OATP1B1 forced-expression cells, immortalized human hepatocytes, primary cultured human hepatocytes, freshly isolated human hepatocytes, cryopreserved human hepatocytes, and sandwich-cultured human hepatocytes or be cells overexpressing a protein consisting of the amino acid sequence shown in SEQ ID NO: 1 in the cell membrane or cells transformed with a DNA consisting of the nucleotide sequence shown in SEQ ID NO: 2.

The present invention further provides a use of a kit including dichlorofluorescein and positive cells expressing OATP1B1 in measurement of the expression level of OATP1B1 in test cells. It is preferable that the positive cells expressing OATP1B1 in the kit be selected from the group consisting of OATP1B1 forced-expression cells, immortalized human hepatocytes, primary cultured human hepatocytes, freshly isolated human hepatocytes, cryopreserved human hepatocytes, and sandwich-cultured human hepatocytes or be cells overexpressing a protein consisting of the amino acid sequence shown in SEQ ID NO: 1 in the cell membrane or cells transformed with a DNA consisting of the nucleotide sequence shown in SEQ ID NO: 2.

Advantageous Effects of Invention

A compound that enhances or inhibits the transport activity of OATP1B1 can be detected safely, inexpensively, and easily to operate with sensitivity comparable to that of an RI method by using dichlorofluorescein, which has been proved as an excellent substrate of OATP1B1. The compound selected by the screening method of the present invention is expected to be capable of controlling the in vivo pharmacokinetics, such as blood level, of a drug serving as a substrate of OATP1B1. It is also possible to predict OATP1B1-mediated drug interaction potential of a test compound by the screening method of the present invention.

The present invention can also provide a method for measuring the expression level of OATP1B1 safely, inexpensively, and easily to operate with sensitivity comparable to that of an RI method. It is believed that the measurement of the expression level of OATP1B1 is useful for, for example, evaluation of an activity of cells, such as hepatocytes, expressing OATP1B1 and comparison of activities of hepatocytes of different lots.

BRIEF DESCRIPTION OF DRAWINGS

FIG. 1 includes graphs showing substrate specificities of various fluorescein derivatives.

DESCRIPTION OF EMBODIMENTS

Figure 2:
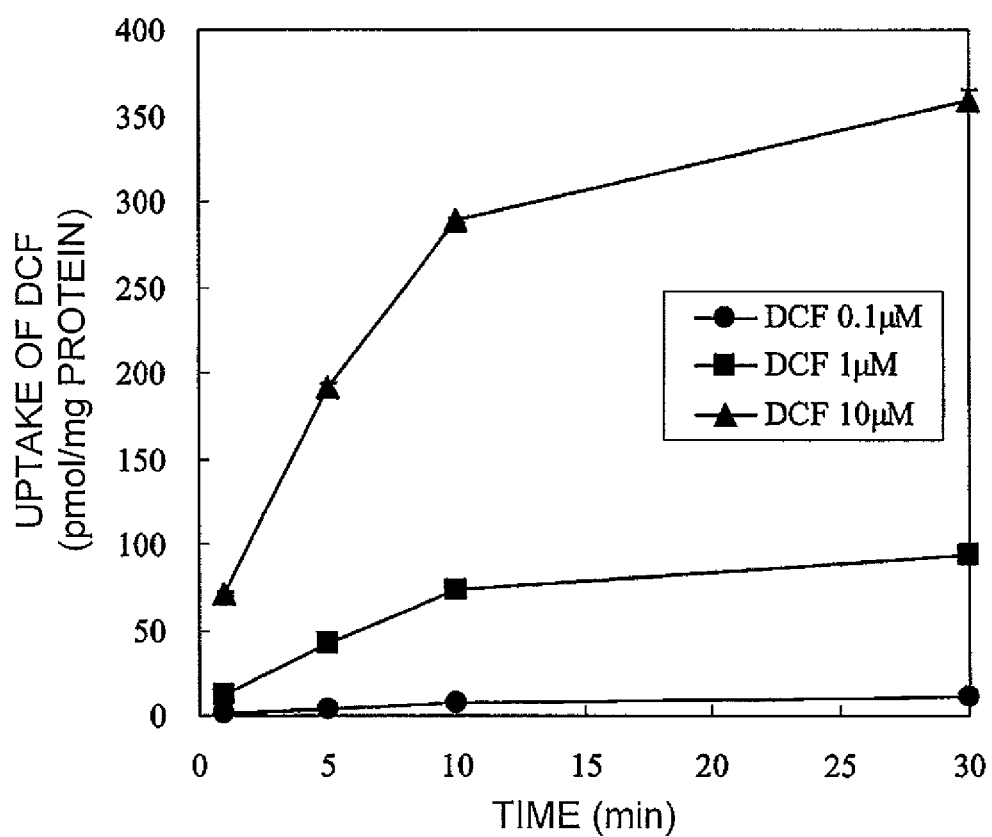
FIG. 2 is a graph showing time profiles of the uptake of dichlorofluorescein (DCF) by OATP1B1.

OATP1B1 in the present invention is mainly expressed in the cell membrane of human hepatocytes and is one of organic anion transporter proteins (organic anion-transporting polypeptide: OATP) having an activity of uptake of anionic compounds into cells (transport activity) and is also called OATP-C, OATP2, or LST-1. Examples of the OATP1B1 protein include that consisting of the amino acid sequence shown in SEQ ID NO: 1, and proteins including amino acid sequences having substitution, deletion, or addition of one or two to nine amino acid residues in the above amino acid sequence and having the function of OATP1B1 are also encompassed in the present invention. Examples of DNA encoding the OATP1B1 protein include that consisting of the nucleic acid sequence shown in SEQ ID NO: 2, and DNAs including nucleic acid sequences having substitution, deletion, or addition of one or 2 to 50 nucleotides in the above nucleic acid sequence and encoding proteins having the function of OATP1B1 are also encompassed in the present invention.

The dichlorofluorescein (DCF) in the present invention is a derivative of a fluorescent compound, fluorescein, and can be commercially available. It has not been known until now that DCF can be a substrate of an organic anion-transporting polypeptide.

The screening method of the present invention is a method of screening for a compound that enhances or inhibits the transport activity of OATP1B1, using dichlorofluorescein and preferably includes the following steps.

The first step of the screening method of the present invention is a step of preparing cells expressing OATP1B1. The cells expressing OATP1B1 are cells functionally expressing OATP1B1 in the cell membrane. The functionally expressing means that OATP1B1 is expressed in the cell membrane in a state having a transport activity of an anionic compound. The OATP1B1-expressing cells are not specifically limited, and examples thereof include immortalized cell lines expressing OATP1B1, artificially modified cell lines expressing OATP1B1, and cell lines immortalized with viruses and expressing OATP1B1. In addition, a human-derived cell line expressing OATP1B1 and a transgenic cell line highly expressing OATP1B1 are preferably used.

In particular, the OATP1B1-expressing cells used in the screening method of the present invention are preferably primary cultured cells or an established or unestablished cell line expressing OATP1B1, such as OATP1B1 forced-expression cells, immortalized human hepatocytes, primary cultured human hepatocytes, freshly isolated human hepatocytes, cryopreserved human hepatocytes, and sandwich-cultured human hepatocytes. Herein, the OATP1B1 forced-expression cell is a cell introduced with a gene or nucleotide encoding an OATP1B1 protein or peptide by a gene engineering technique and functionally expressing the OATP1B1 protein or peptide.

Such a forced-expression cell is, for example, preferably a cell overexpressing a protein consisting of the amino acid sequence shown in SEQ ID NO: 1 in the cell membrane or a cell transformed with a DNA consisting of the nucleotide sequence shown in SEQ ID NO: 2. The overexpression of OATP1B1 may be either a transient expression or stable expression, and cells stably expressing OATP1B1 are more preferably used in view of reproducibility. Similarly, the transformed cell may be either a transiently or stably transformed cell, and stably transformed cells are more preferably used in view of reproducibility.

The host cell for forced expression is not specifically limited, and mammal cells, such as HEK-293 cells, or *Xenopus oocytes* are preferably used from the simplicity of handling. The technique of gene transfer is generally known. For example, an objective DNA is amplified by, for example, PCR using a human liver cDNA as a template and appropriate primers so as to clone the full length of the nucleotide sequence shown in SEC ID NO: 2; the DNA is inserted into a vector having an appropriate expression promoter; and the vector is introduced into cells by a method such as calcium phosphate transfection, lipofection, or microinjection. The transformed cells can be selected with an appropriate selective medium.

The second step of the screening method of the present invention is a step of bringing dichlorofluorescein and a test compound into contact with the cells. The bringing dichlorofluorescein and a test compound into contact with cells refers to adding the both simultaneously or sequentially to a culture medium or buffer for the cells to contact the both with the cells. A concentration of dichlorofluorescein of 0.1 μM or more gives sufficient detection sensitivity, and the concentration may be appropriately adjusted within a range of 0.1 to 1000 μM for example. Meanwhile, the concentration of the test compound varies depending on the compound and, in general, may be appropriately adjusted within a range of 1 nM to 1 mM. The time for contacting with the cells may be 1 to 30 minutes and is preferably in the time range in which the uptake of dichlorofluorescein linearly increases.

After the contact of the dichlorofluorescein and the test compound with the cells, the cells are preferably washed for removing the fluorescent compound not taken up by the cells. The washing may be generally performed with a buffer such as PBS or Krebs-Henseleit (KH) buffer at a temperature of 1 to 10° C. one to three times.

The third step of the screening method of the present invention is a step of measuring the fluorescence intensity of dichlorofluorescein taken up by the cells. The dichlorofluorescein taken up by the cells can be collected in a solution by solubilizing the cells. Examples of the solubilization of cells include treatment with an aqueous NaOH solution. The fluorescence intensity of the solution containing collected dichlorofluorescein is measured with a fluorophotometer at an excitation wavelength of 450 to 550 nm and a fluorescence wavelength of 500 to 600 nm. In order to convert the measured fluorescence intensity into the amount (such as molar number) of the fluorescent compound, it is preferable to form a calibration curve in advance. In addition, in order to standardize the incorporated fluorescent compound, it is preferable to convert the amount of the fluorescent compound into the amount per cell or per unit protein.

The fourth step of the screening method of the present invention is a step of determining the test compound as a compound that enhances the transport activity of OATP1B1 in a case that the measured fluorescence intensity is higher than that when the test compound is not present and determining the test compound as a compound that inhibits the transport activity of OATP1B1 in a case that the measured fluorescence intensity is lower than that when the test compound is not present. The case that the measured fluorescence intensity is higher than that when the test compound is not present means that the uptake of dichlorofluorescein into the cells is increased by the presence of the test compound, and it is therefore believed that the test compound enhances the transport activity of OATP1B1. On the other hand, the case that the measured fluorescence intensity is lower than that when the test compound is not present means that the uptake of dichlorofluorescein into the cells is decreased by the presence of the test compound, and it is therefore believed that the test compound inhibits the transport activity of OATP1B1.

A compound that enhances the transport activity of OATP1B1 can be used for normalization of genetic polymorphism accompanied by decrease in function of OATP1B1. In addition, it is possible to enhance the excretion of xenobiotics that are transported by OATP1B1. On the other hand, a compound that inhibits the transport activity of OATP1B1 causes drug interaction with a selective substrate of OATP1B1, and, therefore, selection of a compound that does not inhibit the transport activity of OATP1B1 leads to creation of a pharmaceutical agent that is low in risk of drug interaction.

The present invention also provides a use of dichlorofluorescein in measurement of the expression level of OATP1B1. It is preferable to specify the dichlorofluorescein to be used for measuring the expression level of OATP1B1, that is, it is preferable, for example, that dichlorofluorescein be packaged together with a manual describing, for example, a method for measuring the expression level of OATP1B1.

The method of the present invention of measuring the expression level of OATP1B1 in test cells includes a step of bringing dichlorofluorescein into contact with test cells; a step of measuring the fluorescence intensity of dichlorofluorescein taken up by the test cells; and a step of evaluating the expression level of OATP1B1 in the test cells based on the measured fluorescence intensity. These steps are equivalent to the above-described steps. It is preferable that the measured fluorescence intensity be first converted into the amount of the fluorescent compound based on a calibration curve and then standardized into the compound amount per cell or per unit protein. The prepared standardized data can be compared to those in other cells and can be used in selection of cells that express a relatively large or small amount of OATP1B1.

In the measurement method of the present invention, it is preferable to relatively evaluate the expression level of OATP1B1 in test cells, using positive cells expressing OATP1B1 as a control. It is preferable that the positive cells expressing OATP1B1 be selected from the group consisting of OATP1B1 forced-expression cells, immortalized human hepatocytes, primary cultured human hepatocytes, freshly isolated human hepatocytes, cryopreserved human hepatocytes, and sandwich-cultured human hepatocytes or be cells overexpressing a protein consisting of the amino acid sequence shown in SEQ ID NO: 1 in the cell membrane or cells transformed with a DNA consisting of the nucleotide sequence shown in SEQ ID NO: 2.

The present invention also provides a use of a kit including dichlorofluorescein and positive cells expressing OATP1B1 in measurement of the expression level of OATP1B1 in test cells. It is preferable that the positive cells expressing OATP1B1 in the kit be selected from the group consisting of OATP1B1 forced-expression cells, immortalized human hepatocytes, primary cultured human hepatocytes, freshly isolated human hepatocytes, cryopreserved human hepatocytes, and sandwich-cultured human hepatocytes or be cells overexpressing a protein consisting of the amino acid sequence shown in SEQ ID NO: 1 in the cell membrane or cells transformed with a DNA consisting of the nucleotide sequence shown in SEQ ID NO: 2.

The kit optionally includes a medium for culturing cells, a buffer for being added to cells or washing cells, a reagent for measuring the amount of a protein, and other components.

EXAMPLES

Example 1

Investigation of Substrate Specificities of Various Fluorescein Derivatives

Various fluorescent dyes, i.e., the following fluorescein derivatives, were each investigated for adaptability as a substrate of OATPs.

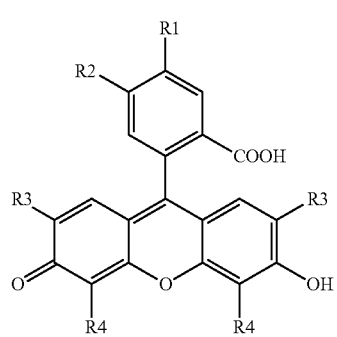

[Chemical Formula 1]

TABLE 1

| Fluorescein derivative | $R_1$ | $R_2$ | $R_3$ | $R_4$ |
|---|---|---|---|---|
| Fluorescein (FL) | H | H | H | H |
| Dichlorofluorescein (DCF) | H | H | Cl | H |
| Carboxydichlorofluorescein (CDCF) | $R_1$ = COOH, $R_2$ = H or $R_1$ = H, $R_2$ = COOH | | Cl | H |
| Oregon Green (Oregon Green) | H | H | F | H |
| 5-Carboxyfluorescein (5-CFL) | COOH | H | H | H |
| 6-Carboxyfluorescein (6-CFL) | H | COOH | H | H |
| Calcein (Calcein) | H | H | H | $CH_2N(CH_2COOH)_2$ |
| Biscarboxyethyl carboxyfluorescein (BCECF) | $R_1$ = COOH, $R_2$ = H or $R_1$ = H, $R_2$ = COOH | | $(CH_2)_2COOH$ | H |

Complementary DNAs of OATP1B1, OATP1B3, and OATP2B1 (respectively shown by SEQ ID NOs: 2, 3, and 4) were cloned by RT-PCR using human liver total RNA (Invitrogen Corporation) as a template and the following primers:

```
Primers for OATP1B1
                              (SEQ ID NO: 5)
sense primer:       CGTCCGACTTGTTGCAGTTG (SEQ ID NO: 6)
antisense primer:   AACACAGAAGCAGAAGTGGC Primers for OATP1B3
                              (SEQ ID NO: 7)
sense primer:       TAACATCAGAAAAAGGATGGACTTG (SEQ ID NO: 8)
antisense primer:   TGCAATGTTAGTTGGCAGCA Primers for OATP2B1
                              (SEQ ID NO: 9)
sense primer:       CTGAGAAGATTTGCTTCCTC (SEQ ID NO: 10)
antisense primer:   ACTGCTGTGGCTGCTACTCT
```

Expression vectors, pcDNA3.1 vectors (Invitrogen Corporation), carrying the resulting genes were respectively introduced into HEK-293 cells by lipofection using Lipofectamin 2000 (Invitrogen Corporation). The cells were cultured in Hygromycin-containing selective media to produce HEK-293 cells forcedly expressing OATP1B1, OATP1B3, and OATP2B1, respectively.

The above cells were seeded in a poly-D-lysine-coated dish at $4 \times 10^5$ cells/well. The medium was replaced with a KH buffer, and various fluorescent dyes dissolved in DMSO were added to the respective HEK-293 cells such that the final concentration in the KH buffer was 1 μM, followed by incubation at 37° C. for 5 minutes. Subsequently, the cells were washed with an ice-cold KH buffer three times and were then solubilized with an aqueous 0.1 N NaOH solution, and the fluorescence intensity of the fluorescent dye taken up by the cells was measured (excitation wavelength: 490 nm, fluorescence wavelength: 515 nm).

In order to quantitatively measure the amount of fluorescent compound taken up by the cells, a calibration curve showing the fluorescence intensity per unit fluorescent compound was prepared in advance. Based on this calibration curve, the measured fluorescence intensity was converted into the fluorescent compound per well (pmol/well or μL/well), which was divided by the total protein amount (mg protein/well) of the solubilized cells (standardization) to convert into the fluorescent compound amount per unit protein (pmol/mg protein or μL/mg protein).

The results are shown in FIG. 1(a). As obvious from FIG. 1(a), a combination of dichlorofluorescein (DCF) and OATP1B1 showed the highest uptake among the combinations of fluorescent dye and transporters tested. The results suggest that DCF is an excellent substrate for OATP1B1. For reference, the substrate specificities of various fluorescein derivatives on OAT1 and OATS were also investigated by the same method. The results are shown in FIG. 1(b). It was proved by FIG. 1(b) that as described in Non Patent Literature 4, 6-CFL is a satisfactory substrate for OAT1 and also that DCF is not a satisfactory substrate for both OAT1 and OAT3. These results also proved that the combination of DCF and OATP1B1 has specificity.

Example 2

Time Profiles of the Uptake of DCF by OATP1B1

As in Example 1, HEK-293 cells forcedly expressing OATP1B1 were prepared and were seeded in a poly-D-lysine-coated dish at $4 \times 10^5$ cells/well. The medium was replaced with a KH buffer, and DCF dissolved in DMSO was added to the cells such that the final concentrations in the KH buffer were 0.1 µM, 1 µM, and 10 µM, followed by incubation at 37° C. for 0 to 30 minutes. The cells were sampled at the incubation times of 1 min, 5 min, 10 min, and 30 min, washed with an ice-cold KH buffer three times, and then solubilized with an aqueous 0.1 N NaOH solution, and the fluorescence intensity of the fluorescent dye taken up by the cells was measured as in Example 1 (excitation wavelength: 490 nm, fluorescence wavelength: 515 nm).

The results are shown in FIG. 2. It was revealed from FIG. 2 that the uptake amount of DCF by the HEK-293 cells forcedly expressing OATP1B1 into the cells increases over time and depends on the concentration of added DCF.

Example 3

Kinetic Analysis of DCF Uptake by OATP1B1

As in Example 1, HEK-293 cells forcedly expressing OATP1B1 were prepared and were seeded in a poly-D-lysine-coated dish at $4 \times 10^5$ cells/well. The medium was replaced with a KH buffer, and DCF dissolved in DMSO was added to the cells such that the final concentrations in the KH buffer were 0.1 to 100 µM, followed by incubation at 37° C. for 5 minutes. The uptake velocities at 0.1 µM, 0.3 µM, 1 µM, 3 µM, 10 µM, 30 µM, and 100 µM concentrations of DCF were plotted, and analyzed by Michaelis-Menten Plot.

Figure 3:
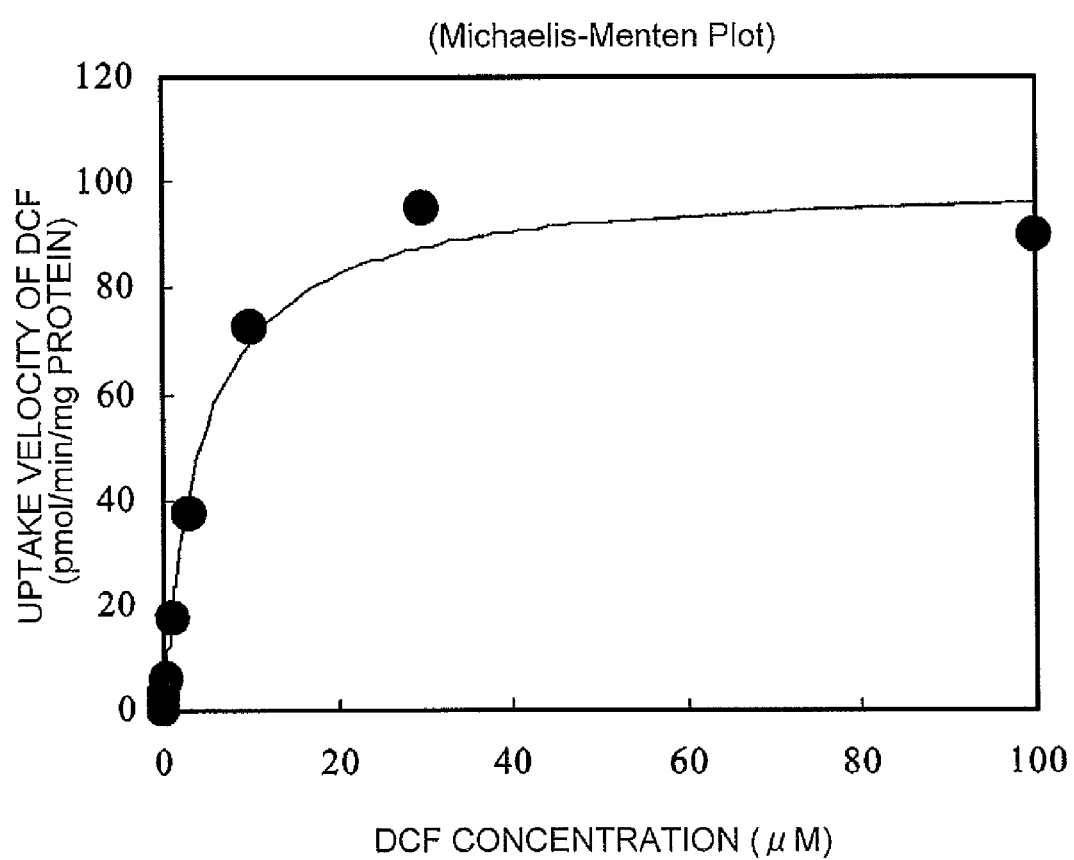
FIG. 3 is a graph showing a kinetic analysis of DCF uptake by OATP1B1.

The results are shown in FIG. 3. The $K_m$ and $V_{max}$ were calculated by the following Michaelis-Menten equation. As a result, $V_{max}$ was 131.6 (pmol/min/mg protein), and $K_m$ was 7.22 (µM). Each parameter represents the mean value of four independent experiments. It was revealed that DCF is a satisfactory substrate for OATP1B1.

$$v = V_{max} \cdot S/(K_m + S)$$

Example 4

Effect of Known OATP Inhibitors on OATP1B1-Mediated Uptake of DCF

As in Example 1, HEK-293 cells forcedly expressing OATP1B1 were prepared and were seeded in a poly-D-lysine-coated dish at $4 \times 10^5$ cells/well. DCF (in 0.1% DMSO, final concentration: 3 µM) and a predetermined concentration of a known OATP1B1 inhibitor were added to the cells, followed by incubation at 37° C. for 5 minutes. As the known OATP1B1 inhibitors, rifampicin (Rif: 10 µM), bromosulfophthalein (BSP: 10 µM), cyclosporine A (Cys A: 10 µM), estradiol-17β-D-glucuronide (EG: 10 and 30 µM), and estrone-3-sulfate (ES: 10 and 30 µM) were used. After incubation, the cells were washed with an ice-cold KH buffer three times, and then solubilized with an aqueous 0.1 N NaOH solution, and the fluorescence intensity of DCF taken up by the cells was measured as in Example 1 (excitation wavelength: 490 nm, fluorescence wavelength: 515 nm).

Figure 4:
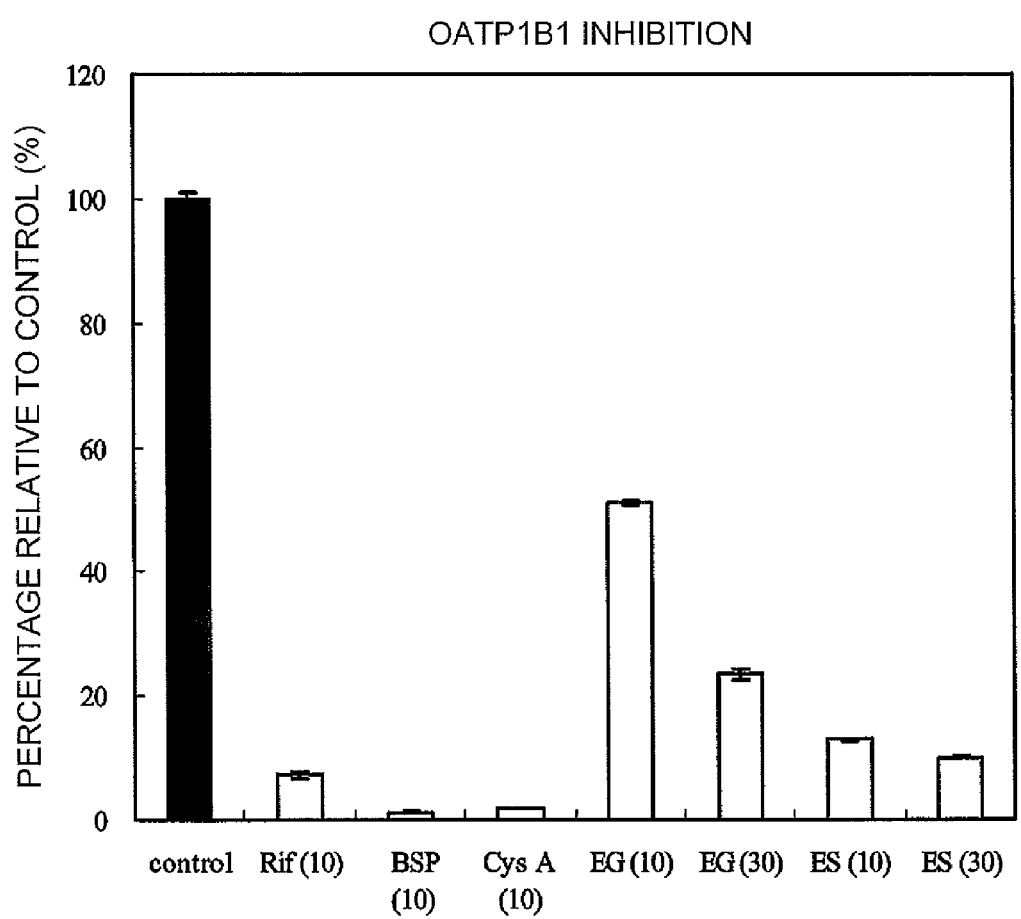
FIG. 4 is a graph showing effect of known OATP inhibitors on OATP1B1-mediated uptake of DCF.

The results are shown in FIG. 4. It was revealed from FIG. 4 that the OATP1B1-mediated uptake of DCF was reduced in cells added with the known OATP1B1 inhibitors, compared to a control not added with any inhibitor. That is, the DCF uptake by HEK-293 cells was inhibited by the known OATP1B1 inhibitor. It was also revealed that this inhibition depends on the concentrations of inhibitors, estradiol-17β-D-glucuronide and estrone-3-sulfate. It was proved that the DCF uptake is mediated by OATP1B1 forcedly expressed in HEK-293 cells.

Example 5

Comparison of $K_i$ Values Between DCF Method and Conventional RI Method

As in Example 1, HEK-293 cells forcedly expressing OATP1B1 were prepared and were seeded in a poly-D-lysine-coated dish at $4 \times 10^5$ cells/well. In the DCF method, as in Example 4, DCF (in 0.1% DMSO, final concentration: 3 µM) and a predetermined concentration of a known OATP inhibitor were added to the cells, the cells were incubated at 37° C. for 5 minutes, and the fluorescence intensity of DCF taken up by the cells was measured (excitation wavelength: 490 nm, fluorescence wavelength: 515 nm). In the conventional RI method, radiolabeled estradiol-17β-D-glucuronide (EG) was used. As in DCF, radiolabeled EG (in 0.1% DMSO, final concentration: 0.01 µM) and a predetermined concentration of a known OATP inhibitor were added to the cells, and the cells were incubated at 37° C. for 5 minutes. Subsequently, the cells were washed with an ice-cold KH buffer three times and then solubilized with an aqueous 0.1 N NaOH solution, and after neutralization with an aqueous 1 N HCl solution, the radioactivity taken up by the cells was measured. As the inhibitor, the compounds shown in the following table were used. The $K_i$ values in the DCF method and the conventional RI method were calculated, and a correlation therebetween was investigated.

TABLE 2

| | | Ki (µM) | |
|---|---|---|---|
| | Compound | DCF | EG |
| 1 | ES | 0.079 | 0.078 |
| 2 | BSP | 0.092 | 0.073 |
| 3 | Cyclosporin A | 0.18 | 0.13 |
| 4 | Rifampicin | 0.26 | 0.29 |
| 5 | Ritonavir | 0.62 | 0.55 |
| 6 | Tacrolimus | 1.27 | 0.89 |
| 7 | Erythromycin | 6.99 | 4.14 |
| 8 | Taurocholic acid | 8.68 | 17.5 |
| 9 | Ketoconazole | 15.6 | 12.2 |
| 10 | Verapamil | 21.8 | 23.9 |
| 11 | Probenecid | 41.9 | 73.4 |
| 12 | Cimetidine | >300 | >300 |
| 13 | Methotrexate | >300 | >300 |

Figure 5:
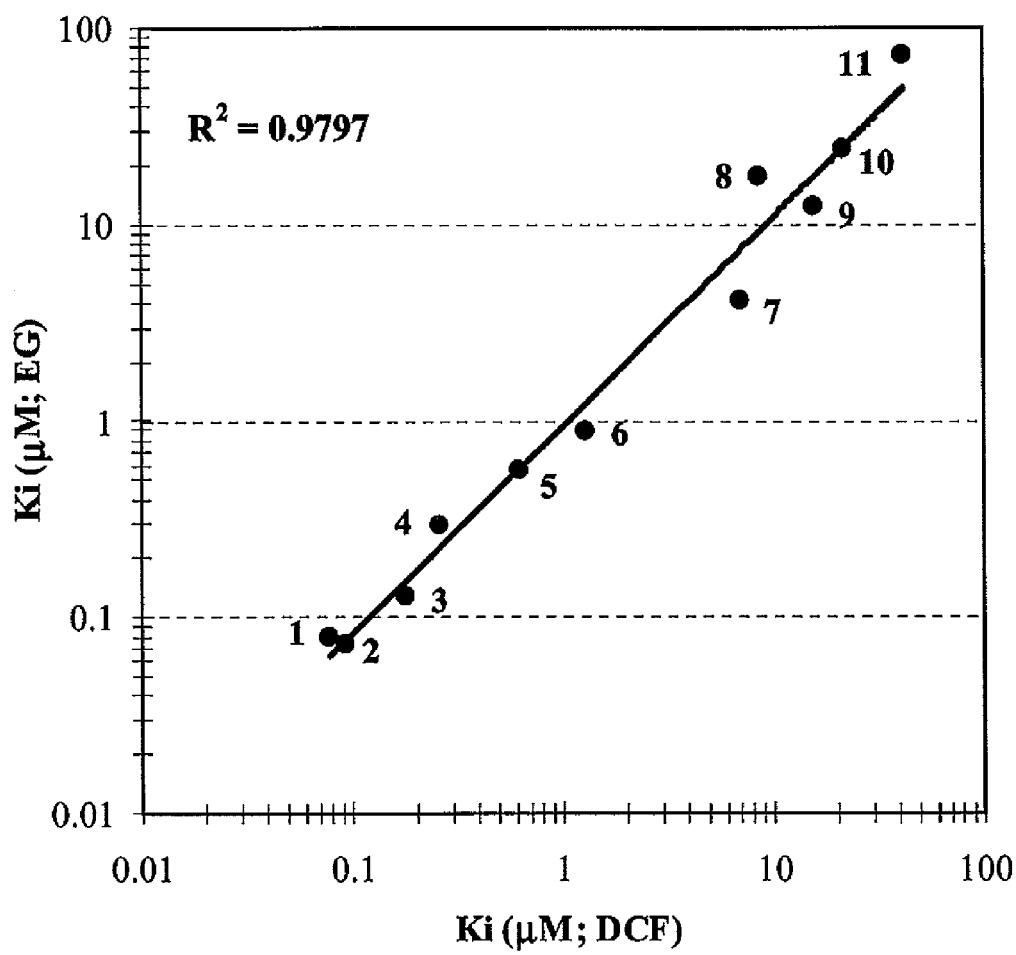
FIG. 5 is a graph showing comparison of $K_i$ values between a DCF method and a known RI method.

The results are shown in FIG. 5. As obvious from FIG. 5, there is a very high correlation between the $K_i$ value from the DCF method and the $K_i$ value from the conventional RI method ($R^2=0.9797$). It was proved from the results that inhibitory effect on OATP1B1 can be evaluated using DCF as the substrate and that DCF method can provide inhibition constants equivalent to those from the conventional RI method.

Example 6

Time/Temperature-Dependent Uptake of DCF by Human Hepatocytes

Cryopreserved human hepatocytes and cryopreserved hepatocytes recovery medium (CHRM) were purchased from Invitrogen Corporation. The cryopreserved human hepatocytes were thawed in a water bath at 37° C. and were added to the CHRM prewarmed at 37° C. After centrifugation at room temperature, the supernatant was discarded, and a hepatocyte suspension at $1\times10^6$ cells/mL was prepared in ice-cold KH buffer and stored on ice. A DCF solution was prepared by dissolving DCF in a KH buffer at a final concentration 20 μM. The hepatocyte suspension was preincubated in a water bath at 37° C. for 2 minutes before the start of uptake reaction, and the DCF solution prewarmed at 37° C. was added thereto in the same volume as that of the hepatocyte suspension to start the reaction. Similarly, also at 4° C., the DCF solution stored on ice in advance was added to the hepatocyte suspension stored on ice in the same volume as that of the hepatocyte suspension to start the reaction. The hepatocytes were incubated at 37° C. and 4° C., respectively, for 0 to 5 minutes. The cells were sampled at the incubation times of 0.5 min, 2 min, and 5 min, and the hepatocytes were separated from the DCF solution by an oil spin method (e.g., Yoshihisa SHITARA, et al., JOURNAL OF PHARMACOLOGY AND EXPERIMENTAL THERAPEUTICS, 304: 610-616, 2003). Specifically, 80 μL of the hepatocyte suspension was collected and added to a centrifugal tube containing 50 μL of oil (specific gravity: 1.015, Sigma-Aldrich Co.) and 100 μL of an aqueous 2 N NaOH solution under the oil layer, and centrifugation was performed at 10,000 g for 20 seconds. By the centrifugation, the hepatocytes passed through the oil layer and were solubilized with an aqueous 2 N NaOH solution. Subsequently, the fluorescence intensity of DCF taken up by the cells was measured as in Example 1 (excitation wavelength: 490 nm, fluorescence wavelength: 515 nm).

Figure 6:
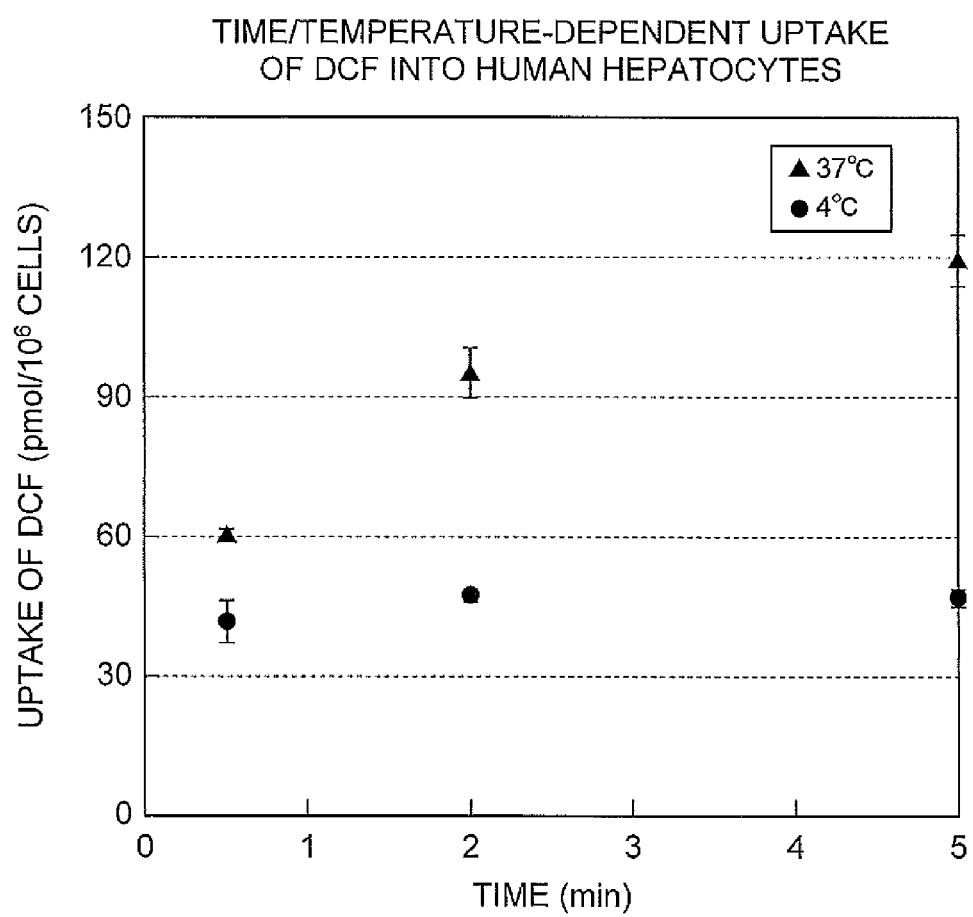
FIG. 6 is a graph showing time/temperature-dependent uptake of DCF by human hepatocytes.

The results are shown in FIG. 6. Since transporters expressed on the cell surface membrane of hepatocytes do not function at 4° C., the measured uptake of fluorescent compound, DCF, at 4° C. is believed to be transporter-independent uptake (nonspecific binding to membrane surface or passive diffusion). Since the transporter functions at 37° C., the difference between the DCF uptake at 37° C. and 4° C. is believed to be uptake mediated by transporters (OATP1B1 and other transporters expressed in the hepatocytes). It was revealed from FIG. 6 that the transporter-mediated uptake of DCF by human hepatocytes at 37° C. increases over time.

Example 7

Kinetic Analysis of DCF Uptake by Human Hepatocytes

Human hepatocytes were prepared as in Example 6, and a hepatocyte suspension was prepared at $1\times10^6$ cells/mL. DCF was dissolved in a KH buffer at final concentrations of 2 μM, 6 μM, 20 μM, 60 μM, 200 μM, 600 μM, and 2000 μM. The hepatocyte suspension was incubated in a water bath at 37° C. for 2 minutes before the start of uptake reaction, and a DCF solution prewarmed at 37° C. was added thereto in the same volume as that of the hepatocyte suspension to start the reaction. The hepatocytes were incubated at 37° C. for 0 to 5 minutes and were sampled at the incubation times of 0.5 min, 2 min, and 5 min, and the hepatocytes were separated from the DCF solution by an oil spin method. The hepatocytes were solubilized with an aqueous 2 N NaOH solution, and the fluorescence intensity of DCF taken up by the cells was measured as in Example 1 (excitation wavelength: 490 nm, fluorescence wavelength: 515 nm). The uptake velocity at each concentration was plotted, the data were analyzed by Michaelis-Menten equation including the term of passive diffusion, and the relationship between the uptake velocity and the uptake clearance of DCF was further analyzed by Eadie-Hofstee plot.

Figure 7:
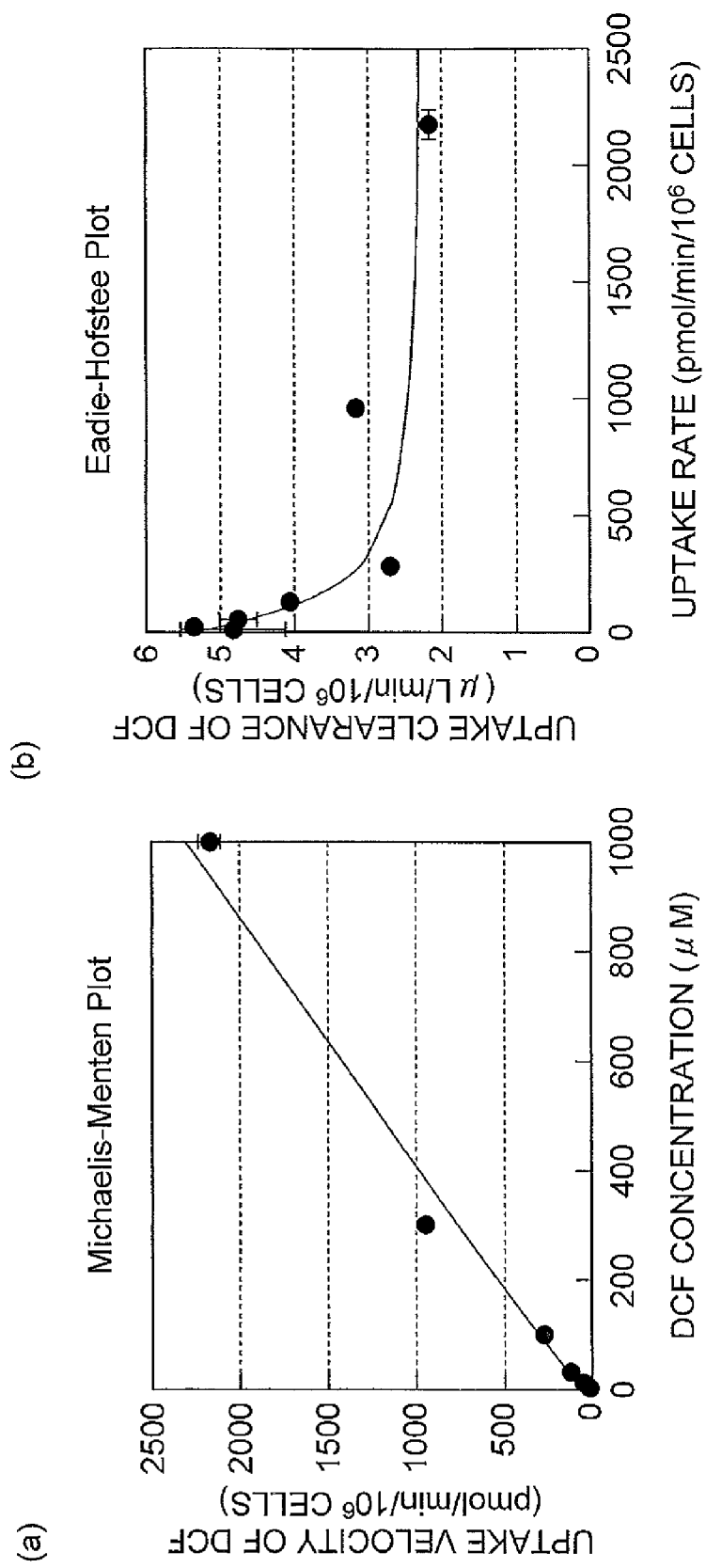
FIG. 7 includes graphs showing a kinetic analysis of DCF uptake by human hepatocytes.

The results are shown in (a) and (b) of FIG. 7. In (b) of FIG. 7, saturation of the uptake of DCF was observed at the higher concentration range corresponding to higher uptake velocity. This result suggests that the uptake of DCF by human hepatocytes is mediated by transporters. Furthermore, in the kinetic analysis, $K_m$, $V_{max}$, and $P_{dif}$ were calculated by the following Michaelis-Menten equation including the term of passive diffusion. As a result, $K_m$ was 38.55 μM, $V_{max}$ was 117.52 pmol/min/$10^6$ cells, and $P_{dif}$ was 2.20 μL/min/$10^6$ cells. It is predicted that the DCF uptake by human hepatocytes is mainly mediated by OATP1B1, from that the $K_m$ value is close to that obtained from the cells forcedly expressing OATP1B1 in Example 3 ($K_m$=7.22 μM) and that as shown in Example 1, among the OATP transporters expressed in human hepatocytes, OATP1B1 showed the highest transport activity on DCF.

$$v=V_{max}\cdot S/(K_m+S)+P_{dif}\cdot S$$

Example 8

Effect of OATP Inhibitor on DCF Uptake by Human Hepatocytes

Human hepatocytes were prepared as in Example 6, and a hepatocyte suspension was prepared at $1\times10^6$ cells/mL. DCF was dissolved in a KH buffer at final concentrations of 20 μM and 2000 μM. A DMSO solution containing a predetermined concentration of a known OATP1B1 inhibitor was added to the KH buffer containing 20 μM of DCF to give an inhibitor solution. As the known OATP1B1 inhibitors, bromosulfophthalein (BSP, final concentration: 10 μM), rifampicin (Rif, final concentration: 10 μM and cyclosporine A (Cys A, final concentration: 10 μM) were used. In addition, a positive control not containing any inhibitor, a negative control (4° C.) not containing any OATP1B1 inhibitor and being investigated at 4° C., and a control (DCF (1000)) containing a high concentration (final concentration: 1000 μM) in of DCF instead of inhibitors were each prepared by adding DMSO to a KH buffer containing a predetermined concentration of DCF. The hepatocyte suspension was incubated in a water bath at 37° C. for 2 minutes before the start of uptake reaction, and a solution containing DCF prewarmed at 37° C. was added thereto in the same volume as that of the hepatocyte suspension to start the reaction. The hepatocytes were incubated at 37° C. for 0 to 5 minutes and were sampled at the incubation times of 0.5 min, 2 min, and 5 min, and the hepatocytes were separated from the DCF solution by an oil spin method. The hepatocytes were solubilized with an aqueous 2 N NaOH solution, and the fluorescence intensity of DCF taken up by the cells was measured as in Example 1 (excitation wavelength: 490 nm, fluorescence wavelength: 515 nm).

Figure 8:
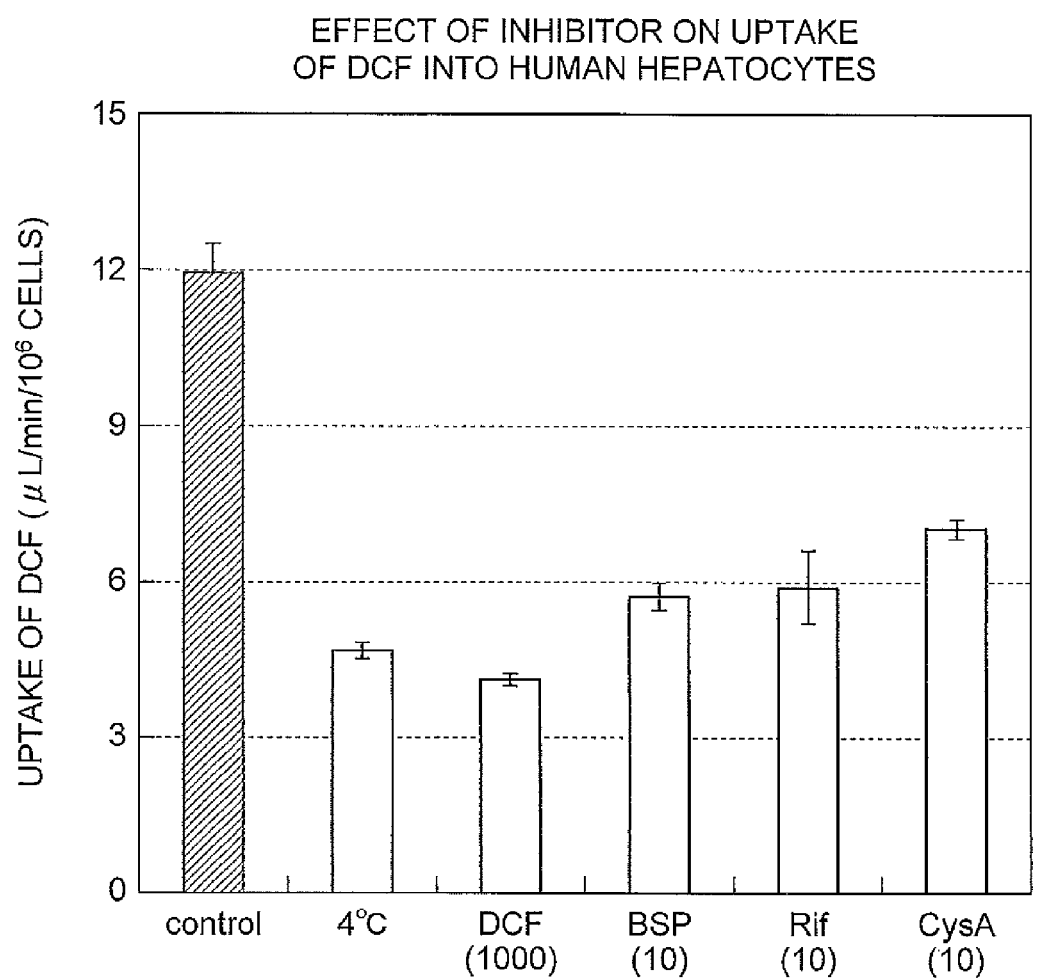
FIG. 8 is a graph showing effect of OATP inhibitors on DCF uptake by human hepatocytes.

The results are shown in FIG. 8. In FIG. 8, it is believed that the difference between uptake of the positive control and 4° C., both not containing any inhibitor, is the uptake quantity of DCF mediated by transporters. On the other hand, the control containing 1000 μM of DCF showed a fluorescence intensity level comparable to the uptake at 4° C., and no transporter-mediated uptake was observed. This result is believed to result from saturation of the transporters by 1000 μM of DCF. In addition, it was revealed that the DCF uptake was reduced by each of OATP1B1 inhibitors: BSP, Rif, and Cys A to the level comparable to the uptake at 4° C. That is, the DCF uptake by human hepatocytes was inhibited by the known OATP1B1 inhibitors. It was confirmed by this result that the DCF uptake into human hepatocytes is mainly mediated by OATP1B1.

INDUSTRIAL APPLICABILITY

A compound that enhances or inhibits the transport activity of OATP1B1 can be detected safely, inexpensively, and easily to operate with sensitivity comparable to that of an RI method by using dichlorofluorescein, which has been proved as an excellent substrate of OATP1B1. The compound selected by the screening method of the present invention is expected to be capable of controlling the in vivo pharmacokinetics, such as blood level, of a drug serving as a substrate of OATP1B1. It is also possible to predict OATP1B1-mediated drug interaction potential of a test compound by the screening method of the present invention.

The present invention can also provide a method for measuring the expression level of OATP1B1 safely, inexpensively, and easily to operate with sensitivity comparable to that of an RI method. It is believed that the measurement of the expression level of OATP1B1 is useful for, for example, evaluation of an activity of cells, such as hepatocytes, expressing OATP1B1 and comparison of activities of hepatocytes of different lots.

SEQUENCE LISTING

The invention claimed is:

1. A method of screening for a compound that enhances or inhibits a transport activity of OATP1B1, comprising:
   a step of preparing a cell expressing OATP1B1;
   a step of bringing dichlorofluorescein and a test compound into contact with the cell;
   a step of measuring a fluorescence intensity of dichlorofluorescein taken up by the cell; and
   a step of determining the test compound as a compound that enhances the transport activity of OATP1B1 in a case that the measured fluorescence intensity is higher than that when the test compound is not present and determining the test compound as a compound that inhibits the transport activity of OATP1B1 in a case that the measured fluorescence intensity is lower than that when the test compound is not present.

2. The method according to claim 1, wherein the cell expressing OATP1B1 is selected from the group consisting of a cell comprising a nucleotide sequence encoding OATP1B1 inserted into a vector having an expression promoter, an immortalized human hepatocyte, a primary cultured human hepatocyte, a freshly isolated human hepatocyte, a cryopreserved human hepatocyte, and a sandwich-cultured human hepatocyte.

3. The method according to claim 1, wherein the cell expressing OATP1B1 is a cell comprising a nucleotide sequence inserted into a vector having an expression promoter, wherein the nucleotide sequence encodes a protein consisting of the amino acid sequence shown in SEQ ID NO: 1.

4. The method according to claim 1, wherein the cell expressing OATP1B1 is a cell transformed with a DNA consisting of the nucleotide sequence shown in SEQ ID NO: 2.

5. A method for measuring an expression level of OATP1B1 in a test cell, comprising:
   a step of bringing dichlorofluorescein into contact with the test cell;
   a step of measuring a fluorescence intensity of dichlorofluorescein taken up by the test cell; and
   a step of evaluating an expression level of OATP1B1 in the test cell based on the measured fluorescence intensity.

6. The method according to claim 5, wherein the expression level of OATP1B1 in the test cell is relatively evaluated using a positive cell expressing OATP1B1 as a control.

7. The method according to claim 6, wherein the positive cell is selected from the group consisting of a cell comprising a nucleotide sequence encoding OATP1B1 inserted into a vector having an expression promoter, an immortalized human hepatocyte, a primary cultured human hepatocyte, a freshly isolated human hepatocyte, a cryopreserved human hepatocyte, and a sandwich-cultured human hepatocyte.

8. The method according to claim 6, wherein the positive cell is a cell comprising a nucleotide sequence inserted into a vector having an expression promoter, wherein the nucleotide sequence encodes a protein consisting of the amino acid sequence shown in SEQ ID NO: 1.

9. The method according to claim 6, wherein the positive cell is a cell transformed with a DNA consisting of the nucleotide sequence shown in SEQ ID NO: 2.

10. A kit comprising dichlorofluorescein and a positive cell expressing OATP1B1.

11. The kit according to claim 10, wherein the positive cell is selected from the group consisting of a cell comprising a nucleotide sequence encoding OATP1B1 inserted into a vector having an expression promoter, an immortalized human hepatocyte, a primary cultured human hepatocyte, a freshly isolated human hepatocyte, a cryopreserved human hepatocyte, and a sandwich-cultured human hepatocyte.

12. The kit according to claim 10, wherein the positive cell is a cell comprising a nucleotide sequence inserted into a vector having an expression promoter, wherein the nucleotide sequence encodes a protein consisting of the amino acid sequence shown in SEQ ID NO: 1.

13. The kit according to claim 10, wherein the positive cell is a cell transformed with a DNA consisting of the nucleotide sequence shown in SEQ ID NO: 2.

* * * * *

```
SEQUENCE LISTING

<160> NUMBER OF SEQ ID NOS: 10

<210> SEQ ID NO 1
<211> LENGTH: 691
<212> TYPE: PRT
<213> ORGANISM: Homo sapiens

<400> SEQUENCE: 1

Met Asp Gln Asn Gln His Leu Asn Lys Thr Ala Glu Ala Gln Pro Ser
1               5                   10                  15

Glu Asn Lys Lys Thr Arg Tyr Cys Asn Gly Leu Lys Met Phe Leu Ala
            20                  25                  30

Ala Leu Ser Leu Ser Phe Ile Ala Lys Thr Leu Gly Ala Ile Ile Met
        35                  40                  45

Lys Ser Ser Ile Ile His Ile Glu Arg Arg Phe Glu Ile Ser Ser Ser
    50                  55                  60

Leu Val Gly Phe Ile Asp Gly Ser Phe Glu Ile Gly Asn Leu Leu Val
65                  70                  75                  80

Ile Val Phe Val Ser Tyr Phe Gly Ser Lys Leu His Arg Pro Lys Leu
                85                  90                  95

Ile Gly Ile Gly Cys Phe Ile Met Gly Ile Gly Val Leu Thr Ala
            100                 105                 110

Leu Pro His Phe Phe Met Gly Tyr Tyr Arg Tyr Ser Lys Glu Thr Asn
        115                 120                 125

Ile Asn Ser Ser Glu Asn Ser Thr Ser Thr Leu Ser Thr Cys Leu Ile
    130                 135                 140

Asn Gln Ile Leu Ser Leu Asn Arg Ala Ser Pro Glu Ile Val Gly Lys
145                 150                 155                 160

Gly Cys Leu Lys Glu Ser Gly Ser Tyr Met Trp Ile Tyr Val Phe Met
                165                 170                 175

Gly Asn Met Leu Arg Gly Ile Gly Glu Thr Pro Ile Val Pro Leu Gly
            180                 185                 190

Leu Ser Tyr Ile Asp Asp Phe Ala Lys Glu Gly His Ser Ser Leu Tyr
        195                 200                 205

Leu Gly Ile Leu Asn Ala Ile Ala Met Ile Gly Pro Ile Ile Gly Phe
    210                 215                 220

Thr Leu Gly Ser Leu Phe Ser Lys Met Tyr Val Asp Ile Gly Tyr Val
225                 230                 235                 240

Asp Leu Ser Thr Ile Arg Ile Thr Pro Thr Asp Ser Arg Trp Val Gly
                245                 250                 255
```

```
Ala Trp Trp Leu Asn Phe Leu Val Ser Gly Leu Phe Ile Ile Ser
            260                 265                 270

Ser Ile Pro Phe Phe Leu Pro Gln Thr Pro Asn Lys Pro Gln Lys
        275                 280                 285

Glu Arg Lys Ala Ser Leu Ser Leu His Val Leu Glu Thr Asn Asp Glu
290                 295                 300

Lys Asp Gln Thr Ala Asn Leu Thr Asn Gln Gly Lys Asn Ile Thr Lys
305                 310                 315                 320

Asn Val Thr Gly Phe Phe Gln Ser Phe Lys Ser Ile Leu Thr Asn Pro
                325                 330                 335

Leu Tyr Val Met Phe Val Leu Leu Thr Leu Leu Gln Val Ser Ser Tyr
            340                 345                 350

Ile Gly Ala Phe Thr Tyr Val Phe Lys Tyr Val Glu Gln Gln Tyr Gly
            355                 360                 365

Gln Pro Ser Ser Lys Ala Asn Ile Leu Leu Gly Val Ile Thr Ile Pro
    370                 375                 380

Ile Phe Ala Ser Gly Met Phe Leu Gly Gly Tyr Ile Ile Lys Lys Phe
385                 390                 395                 400

Lys Leu Asn Thr Val Gly Ile Ala Lys Phe Ser Cys Phe Thr Ala Val
                405                 410                 415

Met Ser Leu Ser Phe Tyr Leu Leu Tyr Phe Phe Ile Leu Cys Glu Asn
            420                 425                 430

Lys Ser Val Ala Gly Leu Thr Met Thr Tyr Asp Gly Asn Asn Pro Val
            435                 440                 445

Thr Ser His Arg Asp Val Pro Leu Ser Tyr Cys Asn Ser Asp Cys Asn
    450                 455                 460

Cys Asp Glu Ser Gln Trp Glu Pro Val Cys Gly Asn Asn Gly Ile Thr
465                 470                 475                 480

Tyr Ile Ser Pro Cys Leu Ala Gly Cys Lys Ser Ser Gly Asn Lys
                485                 490                 495

Lys Pro Ile Val Phe Tyr Asn Cys Ser Cys Leu Glu Val Thr Gly Leu
            500                 505                 510

Gln Asn Arg Asn Tyr Ser Ala His Leu Gly Glu Cys Pro Arg Asp Asp
            515                 520                 525

Ala Cys Thr Arg Lys Phe Tyr Phe Val Ala Ile Gln Val Leu Asn
    530                 535                 540

Leu Phe Phe Ser Ala Leu Gly Gly Thr Ser His Val Met Leu Ile Val
545                 550                 555                 560

Lys Ile Val Gln Pro Glu Leu Lys Ser Leu Ala Leu Gly Phe His Ser
                565                 570                 575

Met Val Ile Arg Ala Leu Gly Gly Ile Leu Ala Pro Ile Tyr Phe Gly
            580                 585                 590

Ala Leu Ile Asp Thr Thr Cys Ile Lys Trp Ser Thr Asn Asn Cys Gly
            595                 600                 605

Thr Arg Gly Ser Cys Arg Thr Tyr Asn Ser Thr Ser Phe Ser Arg Val
    610                 615                 620

Tyr Leu Gly Leu Ser Ser Met Leu Arg Val Ser Ser Leu Val Leu Tyr
625                 630                 635                 640

Ile Ile Leu Ile Tyr Ala Met Lys Lys Tyr Gln Glu Lys Asp Ile
                645                 650                 655

Asn Ala Ser Glu Asn Gly Ser Val Met Asp Glu Ala Asn Leu Glu Ser
            660                 665                 670
```

Leu Asn Lys Asn Lys His Phe Val Pro Ser Ala Gly Ala Asp Ser Glu
        675                 680                 685

Thr His Cys
    690

<210> SEQ ID NO 2
<211> LENGTH: 2076
<212> TYPE: DNA
<213> ORGANISM: Homo sapiens

<400> SEQUENCE: 2

| | | | | | |
|---|---|---|---|---|---|
| atggaccaaa | atcaacattt | gaataaaaca | gcagaggcac | aaccttcaga | gaataagaaa | 60 |
| acaagatact | gcaatggatt | gaagatgttc | ttggcagctc | tgtcactcag | ctttattgct | 120 |
| aagacactag | gtgcaattat | tatgaaaagt | tccatcattc | atatagaacg | gagatttgag | 180 |
| atatcctctt | ctcttgttgg | ttttattgac | ggaagctttg | aaattggaaa | tttgcttgtg | 240 |
| attgtatttg | tgagttactt | tggatccaaa | ctacatagac | caaagttaat | tggaatcggt | 300 |
| tgtttcatta | tgggaattgg | aggtgttttg | actgctttgc | cacatttctt | catgggatat | 360 |
| tacaggtatt | ctaaagaaac | taatatcgat | tcatcagaaa | attcaacatc | gaccttatcc | 420 |
| acttgtttaa | ttaatcaaat | tttatcactc | aatgagcat | cacctgagat | agtgggaaaa | 480 |
| ggttgtttaa | aggaatctgg | gtcatacatg | tggatatatg | tgttcatggg | taatatgctt | 540 |
| cgtggaatag | gggagactcc | catagtacca | ctggggcttt | cttacataga | tgatttcgct | 600 |
| aaagaaggac | attcttcttt | gtatttaggt | atattgaatg | caatagcaat | gattggtcca | 660 |
| atcattggct | ttaccctggg | atctctgttt | tctaaaatgt | acgtggatat | tggatatgta | 720 |
| gatctaagca | ctatcaggat | aactcctact | gattctcgat | gggttggagc | ttggtggctt | 780 |
| aatttccttg | tgtctggact | attctccatt | atttcttcca | taccattctt | tttcttgccc | 840 |
| caaactccaa | ataaaccaca | aaagaaaga | aaagcttcac | tgtctttgca | tgtgctggaa | 900 |
| acaaatgatg | aaaaggatca | aacagctaat | ttgaccaatc | aaggaaaaaa | tattaccaaa | 960 |
| aatgtgactg | gttttttcca | gtcttttaaa | agcatcctta | ctaatcccct | gtatgttatg | 1020 |
| tttgtgcttt | tgacgttgtt | acaagtaagc | agctatattg | gtgcttttac | ttatgtcttc | 1080 |
| aaatacgtag | agcaacagta | tggtcagcct | tcatctaagg | ctaacatctt | attgggagtc | 1140 |
| ataaccatac | ctattttttgc | aagtggaatg | tttttaggag | gatatatcat | taaaaaattc | 1200 |
| aaactgaaca | ccgttggaat | tgccaaattc | tcatgtttta | ctgctgtgat | gtcattgtcc | 1260 |
| ttttacctat | tatatttttt | catactctgt | gaaaacaaat | cagttgccgg | actaaccatg | 1320 |
| acctatgatg | gaaataatcc | agtgacatct | catagagatg | taccactttc | ttattgcaac | 1380 |
| tcagactgca | attgtgatga | aagtcaatgg | gaaccagtct | gtggaaacaa | tggaataact | 1440 |
| tacatctcac | cctgtctagc | aggttgcaaa | tcttcaagtg | gcaataaaaa | gcctatagtg | 1500 |
| ttttacaact | gcagttgttt | ggaagtaact | ggtctccaga | acagaaatta | ctcagcccat | 1560 |
| ttgggtgaat | gcccaagaga | tgatgcttgt | acaaggaaat | tttactttt | tgttgcaata | 1620 |
| caagtcttga | atttattttt | ctctgcactt | ggaggcacct | cacatgtcat | gctgattgtt | 1680 |
| aaaattgttc | aacctgaatt | gaaatcactt | gcactgggtt | tccactcaat | ggttatacga | 1740 |
| gcactaggag | gaattctagc | tccaatatat | tttggggctc | tgattgatac | aacgtgtata | 1800 |
| aagtggtcca | ccaacaactg | tggcacacgt | gggtcatgta | ggacatataa | ttccacatca | 1860 |
| ttttcaaggg | tctacttggg | cttgtcttca | atgttaagag | tctcatcact | tgttttatat | 1920 |
| attatattaa | tttatgccat | gaagaaaaaa | tatcaagaga | aagatatcaa | tgcatcagaa | 1980 |

| | |
|---|---|
| aatggaagtg tcatggatga agcaaactta gaatccttaa ataaaaataa acattttgtc | 2040 |
| ccttctgctg gggcagatag tgaaacacat tgttaa | 2076 |

<210> SEQ ID NO 3
<211> LENGTH: 2109
<212> TYPE: DNA
<213> ORGANISM: Homo sapiens

<400> SEQUENCE: 3

| | |
|---|---|
| atggaccaac atcaacattt gaataaaaca gcagagtcag catcttcaga gaaaagaaa | 60 |
| acaagacgct gcaatggatt caagatgttc ttggcagccc tgtcattcag ctatattgct | 120 |
| aaagcactag gtgaatcat tatgaaaatt ccatcactc aaatagaaag gagatttgac | 180 |
| atatcctctt ctcttgctgg tttaattgat ggaagctttg aaattggaaa tttgcttgtg | 240 |
| attgtatttg taagttactt tggatctaaa ctacacagac cgaagttaat tggaattggt | 300 |
| tgtctcctta tgggaactgg aagtattttg acatctttac cacatttctt catgggatat | 360 |
| tataggtatt ctaaagaaac ccatattaat ccatcagaaa attcaacatc aagtttatca | 420 |
| acctgtttaa ttaatcaaac cttatcattc aatggaacat cacctgagat agtagaaaaa | 480 |
| gattgtgtaa aggaatctgg gtcacacatg tggatctatg tcttcatggg aatatgctt | 540 |
| cgtggcatag gggaaacccc catagtacca ttggggattt catacattga tgtttttgca | 600 |
| aaagaaggac attcttcctt gtatttaggt agtttgaatg caataggaat gattggtcca | 660 |
| gtcattggct ttgcactggg atctctgttt gctaaaatgt acgtggatat tggatatgta | 720 |
| gatctgagca ctatcagaat aactcctaag gactctcgtt gggttggagc ttggtggctt | 780 |
| ggttccttg tgtctggact attttccatt atttcttcca taccattttt tttcttgccg | 840 |
| aaaaatccaa ataaaccaca aaagaaaga aaaatttcac tatcattgca tgtgctgaaa | 900 |
| acaaatgatg atagaaatca aacagctaat ttgaccaacc aaggaaaaaa tgttaccaaa | 960 |
| aatgtgactg gttttttcca gtctttgaaa agcatcctta ccaatcccct gtatgttata | 1020 |
| tttctgcttt tgacattgtt acaagtaagc agctttattg gttctttac ttacgtcttt | 1080 |
| aaatatatgg agcaacagta cggtcagtct gcatctcatg ctaactttt gttgggaatc | 1140 |
| ataaccattc ctacggttgc aactggaatg ttttaggag gatttatcat taaaaaattc | 1200 |
| aaaattgtctt tagttggaat tgccaaattt tcatttctta cttcgatgat atccttcttg | 1260 |
| tttcaacttc tatatttccc tctaatctgc gaaagcaaat cagttgccgg cctaaccttg | 1320 |
| acctatgatg gaaataattc agtggcatct catgtagatg taccactttc ttattgcaac | 1380 |
| tcagagtgca attgtgatga aagtcagtgg gaaccagtct gtgggaacaa tggaataact | 1440 |
| tacctgtcac cctgtctagc aggatgcaaa tcctcaagtg gtattaaaaa gcatacagtg | 1500 |
| ttttataact gtagttgtgt ggaagtaact ggtctccaga acagaaatta ctcagcgcac | 1560 |
| ttgggtgaat gcccaagaga taatacttgt acaaggaaat ttttcatcta tgttgcaatt | 1620 |
| caagtcataa actctttgtt ctctgcaaca ggaggtacca catttatctt gttgactgtg | 1680 |
| aagattgttc aacctgaatt gaaagcgctt gcaatgggtt tccagtcaat ggttataaga | 1740 |
| acactaggag gaattctagc tccaatatat tttggggctc tgattgataa acatgtatg | 1800 |
| aagtggtcca ccaacagctg tggagcacaa ggagcttgta ggatatataa ttccgtattt | 1860 |
| tttgaaggg tctacttggg cttatctata gctttaagat tcccagcact tgttttatat | 1920 |
| attgttttca ttttttgctat gaagaaaaaa tttcaaggaa aagataccaa ggcatcggac | 1980 |

```
aatgaaagaa aagtaatgga tgaagcaaac ttagaattct taaataatgg tgaacatttt    2040
gtaccttctg ctggaacaga tagtaaaaca tgtaatttgg acatgcaaga caatgctgct    2100
gccaactaa                                                            2109

<210> SEQ ID NO 4
<211> LENGTH: 2130
<212> TYPE: DNA
<213> ORGANISM: Homo sapiens

<400> SEQUENCE: 4
atgggaccca ggatagggcc agcgggtgag gtaccccagg taccagacaa ggaaaccaaa      60
gccacaatgg gcacagaaaa cacacctgga ggcaaagcca gcccagaccc tcaggacgtg     120
cggccaagtg tgttccataa catcaagctg ttcgttctgt gccacagcct gctgcagctg     180
gcgcagctca tgatctccgg ctacctaaag agctccatct ccacagtgga gaagcgcttc     240
ggcctctcca gccagacgtc ggggctgctg gcctccttca cgaggtggg gaacacagcc      300 ttgattgtgt ttgtgagcta ttttggcagc cgggtgcacc gaccccgaat gattggctat     360
ggggctatcc ttgtggccct ggcgggcctg ctcatgactc tcccgcactt catctcggag     420
ccataccgct acgacaacac cagccctgag gatatgccac aggacttcaa ggcttccctg     480
tgcctgccca acctcggc ccagcctcg gccccctcca atggcaactg ctcaagctac        540
acagaaaccc agcatctgag tgtggtgggg atcatgttcg tggcacagac cctgctgggc     600
gtgggcgggg tgcccattca gccctttggc atctcctaca tcgatgactt tgcccacaac     660
agcaactcgc cctctacct cgggatcctg tttgcagtga ccatgatggg gccaggcctg      720
gcctttgggc tgggcagcct catgctgcgc ctttatgtgg acattaacca gatgccagaa     780
ggtggtatca gcctgaccat aaaggacccc cgatgggtgg gtgcctggtg gctgggtttc     840
ctcatcgctg ccggtgcagt ggccctggct gccatcccct acttcttctt ccccaaggaa     900
atgcccaagg aaaaacgtga gcttcagttt cggcgaaagg tcttagcagt cacagactca     960
cctgccagga agggcaagga ctctccctct aagcagagcc tggggagtc cacgaagaag     1020 caggatggcc tagtccagat tgcaccaaac ctgactgtga tccagttcat taaagtcttc    1080
cccagggtgc tgctgcagac cctacgccac cccatcttcc tgctggtggt cctgtcccag    1140
gtatgcttgt catccatggc tgcgggcatg gccaccttcc tgcccaagtt cctggagcgc    1200
cagttttcca tcacagcctc ctacgccaac ctgctcatcg gctgcctctc cttcccttcg    1260
gtcatcgtgg gcatcgtggt gggtggcgtc tggtcaagc ggctccacct gggccctgtg     1320
ggatgcggtg ccctttgcct gctggggatg ctgctgtgcc tcttcttcag cctgccgctc    1380
ttctttatcg gctgctccag ccaccagatt gcgggcatca cacaccagac cagtgcccac    1440
cctgggctgg agctgtctcc aagctgcatg gaggcctgct cctgcccatt ggacggcttt    1500
aaccctgtct gcgaccccag cactcgtgtg gaatacatca caccctgcca cgcaggctgc    1560
tcaagctggg tggtccagga tgctctggac aacagccagg ttttctacac caactgcagc    1620
tgcgtggtgg agggcaaccc cgtgctggca ggatcctgcg actcaacgtg cagccatctg    1680
gtggtgccct tcctgctcct ggtcagcctg ggctcggccc tggcctgtct cacccacaca    1740
ccctccttca tgctcatcct aagaggagtg aagaaagaag acaagacttt ggctgtgggc    1800
atccagttca tgttcctgag gattttggcc tggatgccca gccccgtgat ccacggcagc    1860
gccatcgaca ccacctgtgt gcactgggcc ctgagctgtg ggcgtcgagc tgtctgtcgc    1920
tactacaata tgacctgct ccgaaaccgg ttcatcggcc tccagttctt cttcaaaaca    1980
```

```
ggttctgtga tctgcttcgc cttagttttg gctgtcctga ggcagcagga caaagaggca        2040
aggaccaaag agagcagatc cagccctgcc gtagagcagc aattgctagt gtcggggcca        2100
gggaagaagc cagaggattc ccgagtgtga                                         2130
```

```
<210> SEQ ID NO 5
<211> LENGTH: 20
<212> TYPE: DNA
<213> ORGANISM: Artificial
<220> FEATURE:
<223> OTHER INFORMATION: sense primer for OATP1B1

<400> SEQUENCE: 5
cgtccgactt gttgcagttg                                                      20

<210> SEQ ID NO 6
<211> LENGTH: 20
<212> TYPE: DNA
<213> ORGANISM: Artificial
<220> FEATURE:
<223> OTHER INFORMATION: antisense primer for OATP1B1

<400> SEQUENCE: 6
aacacagaag cagaagtggc                                                      20

<210> SEQ ID NO 7
<211> LENGTH: 25
<212> TYPE: DNA
<213> ORGANISM: Artificial
<220> FEATURE:
<223> OTHER INFORMATION: sense primer for OATP1B3

<400> SEQUENCE: 7
taacatcaga aaaggatgg acttg                                                 25

<210> SEQ ID NO 8
<211> LENGTH: 20
<212> TYPE: DNA
<213> ORGANISM: Artificial
<220> FEATURE:
<223> OTHER INFORMATION: antisense primer for OATP1B3

<400> SEQUENCE: 8
tgcaatgtta gttggcagca                                                      20

<210> SEQ ID NO 9
<211> LENGTH: 20
<212> TYPE: DNA
<213> ORGANISM: Artificial
<220> FEATURE:
<223> OTHER INFORMATION: sense primer for OATP2B1

<400> SEQUENCE: 9
ctgagaagat ttgcttcctc                                                      20

<210> SEQ ID NO 10
<211> LENGTH: 20
<212> TYPE: DNA
<213> ORGANISM: Artificial
<220> FEATURE:
<223> OTHER INFORMATION: antisense primer for OATP2B1

<400> SEQUENCE: 10
actgctgtgg ctgctactct                                                      20
```